US012766205B2

(12) United States Patent
Carrara et al.

(10) Patent No.: US 12,766,205 B2
(45) Date of Patent: Oct. 20, 2026

(54) ELEVATOR CAR AND UVC RADIATION DEVICE FOR AN ELEVATOR CAR

(71) Applicant: Inventio AG, Hergiswil (CH)

(72) Inventors: Elena Carrara, Lucerne (CH); Christoph Liebetrau, Menziken (CH); Dominik Schmitt, Root (CH)

(73) Assignee: INVENTIO AG, Hergiswil (CH)

( * ) Notice: Subject to any disclaimer, the term of this patent is extended or adjusted under 35 U.S.C. 154(b) by 801 days.

(21) Appl. No.: 18/251,718

(22) PCT Filed: Nov. 10, 2021

(86) PCT No.: PCT/EP2021/081206
§ 371 (c)(1),
(2) Date: May 4, 2023

(87) PCT Pub. No.: WO2022/101250
PCT Pub. Date: May 19, 2022

(65) Prior Publication Data

US 2024/0009333 A1 Jan. 11, 2024

(30) Foreign Application Priority Data

Nov. 12, 2020 (EP) .................................... 20207300

(51) Int. Cl.
*A61L 2/10* (2026.01)
*A61L 103/75* (2026.01)
*B66B 1/52* (2006.01)

(52) U.S. Cl.
CPC .................. *A61L 2/10* (2013.01); *B66B 1/52* (2013.01); *A61L 2103/75* (2026.01); *A61L 2202/11* (2013.01)

(58) Field of Classification Search
CPC .... A61L 2/10; A61L 2103/75; A61L 2202/11; B66B 1/52; B66B 11/024
See application file for complete search history.

(56) References Cited

U.S. PATENT DOCUMENTS 10,209,005 B2 * 2/2019 Chen .......................... F26B 3/28
2007/0214986 A1 * 9/2007 Gaus ................... B41F 23/0409 101/416.1
2019/0060496 A1 * 2/2019 Tillotson ................... A61L 2/10
(Continued)

FOREIGN PATENT DOCUMENTS

CN 203342072 U 12/2013
CN 111573456 A 8/2020
(Continued)

*Primary Examiner* — Bickey Dhakal
(74) *Attorney, Agent, or Firm* — Shumaker, Loop & Kendrick, LLP

(57) ABSTRACT

An elevator car includes an input device arranged on an interior surface of a first car side wall and a UVC radiation device for irradiating the input device with radiation in the UVC range, the UVC radiation device being arranged on a car ceiling. The UVC radiation device has a plurality of UVC LEDs as radiation sources arranged next to one another in a horizontal direction. The UVC LEDs are arranged in the UVC radiation device such that the emission direction is directed upward. A reflector embodied as a concave mirror is assigned to each radiation source. The UVC LEDs and the reflectors are installed in a box-shaped housing.

14 Claims, 3 Drawing Sheets

(56) References Cited

U.S. PATENT DOCUMENTS

| | | | | |
|---|---|---|---|---|
| 2022/0016288 | A1* | 1/2022 | Huang | A61L 2/24 |
| 2022/0049862 | A1* | 2/2022 | Derwinski | B66B 11/024 |

FOREIGN PATENT DOCUMENTS

| | | | | | |
|---|---|---|---|---|---|
| CN | 111821479 | A | | 10/2020 | |
| DE | 202017100914 | U1 | | 5/2017 | |
| KR | 20060018556 | A | * | 3/2006 | B66B 11/024 |
| KR | 100858142 | B1 | | 9/2008 | |
| KR | 20100089410 | A | | 8/2010 | |
| WO | 2006041431 | A2 | | 4/2006 | |

* cited by examiner

7 UVC LED
11 PRINTED CIRCUIT BOARD

ELEVATOR CAR AND UVC RADIATION DEVICE FOR AN ELEVATOR CAR

FIELD

The invention relates to an elevator car and a UVC radiation device for an elevator car.

BACKGROUND

Elevator systems for conveying people and goods contain elevator cars that can be moved up and down in an elevator shaft. The cars can be moved by means of a drive unit using suspension means, for example in the form of suspension cables or suspension belts. Elevator cars often have car control panels, which are operated by the elevator user via finger touch, for entering a destination floor. As a result, potentially hazardous pathogens, such as currently Covid-19 viruses, can end up on the car control panel and be transmitted to other elevator users. There is therefore the need to disinfect car control panels or other input devices in the car.

SUMMARY

It is an object of the present invention to avoid the disadvantages of the known and, in particular, to create an elevator car with which the input devices in the car can be disinfected in a simple and efficient manner.

This and other objects are achieved according to the invention with an elevator car having the features described herein. The elevator car has at least one input device, arranged on a first car side wall, for generating a control signal to the elevator controller or to another electronic device. The input device can in particular be a car control panel for entering a destination floor, for example a keyboard for entering a selectable destination floor number. The car control panel can additionally or under certain circumstances also alternatively contain keys for entering a closing command to close the door or a hold-open command, an emergency call key, etc. The input device can also, for example, be a device for imparting information to elevator users. Such information can be information about weather, sports results, sports events, stock exchange data, entertainment, comics, etc. Via the input device, information can be provided to the elevator user depending on personal interest by means of a display device. It is also conceivable that, via the input device, persons familiar to the elevator are provided with elevator-specific information. Alternatively or additionally, the elevator specialist can communicate with the elevator via the input device and retrieve statistical information and/or operating data. The input device can, for example, contain keys or buttons that are actuated by pressing. Mechanically operating electrical keys, capacitive keys or piezo keys are known and common. The input device can also contain other manual input means. For example, the input device could also comprise a screen with touch-sensitive input regions (touchscreens).

The generally cuboid elevator car can have a car interior specified by car side walls, a car ceiling and a car floor. The elevator car has a UVC (ultraviolet C wavelength) radiation device for irradiating the input device with radiation in the UVC range for disinfecting the surfaces of the input device touched by elevator users, which radiation device is arranged on the car ceiling. If the input device is arranged on a first car side wall, the UVC radiation device is preferably arranged in a rear region in the vicinity of or adjacent to a second car side wall opposite the first car side wall. The first car side wall and the second car side wall are spaced apart from one another in a longitudinal direction. The side walls connecting the first car side wall and the second car side wall consequently each run in the aforementioned longitudinal direction. Due to the UVC radiation device that is advantageously positioned in or on the car ceiling, any contaminated surfaces on the input device can be disinfected by means of radiation in the UVC range between 200 and 300 nm. In these regions, the germs, more precisely the DNA thereof, absorb the UV light, and permanent damage to the DNA/RNA occurs. This damage, in turn, has the result that the germ cannot propagate and dies. Undesired bacteria, legionellas, viruses, yeasts and fungi on the input device can thus be rendered harmless reliably. A wavelength range between 250 nm and 280 nm is preferred, in which range a particularly effective disinfection can be ensured. The disinfection effect using UVC LEDs can take place at low energy consumption. UVC LEDs furthermore have a long service life and are very low-wear.

The first car side wall can be a vertical wall section adjoining a car door. This wall section, and thus the first car side wall, would thus lie on the same side as the car door. However, the first car side wall can also be a car side wall that preferably runs at right angles to the door-side wall section. However, it would also be conceivable for the first car side wall to form the rear side of the elevator car, which rear side is opposite the front side, defined by the car door, of the elevator car.

For effective irradiation of the input device, the UVC radiation device comprises a plurality of UVC LEDs as radiation sources arranged next to one another in a horizontal direction. The arrangement next to one another relates to the direction that extends transversely to the aforementioned longitudinal direction. The UVC LEDs arranged next to one another form a radiation source row which extends in the transverse direction to the longitudinal direction. A further advantage of this arrangement is the low space requirement of the UVC radiation device.

The respective UVC LEDs can be positioned next to one another in the UVC radiation device in a pointwise arrangement. Each point represents a radiation source. However, the individual points do not have to be points in the geometric sense. The individual UVC LEDs or radiation sources can also be a group of a plurality of UVC radiation-emitting diodes. The UVC LEDs arranged next to one another can be arranged in a row at regular intervals, wherein the distance between two UVC LEDs can, by way of example, be at least 1 cm and preferably at least 2 cm. However, it is also conceivable to adjoin the UVC LEDs to one another in each row so that the UVC LEDs form a linear arrangement.

UVC irradiation is problematic because it is harmful to the health of eyes and also of human skin. The UVC radiation device is therefore preferably controllable in such a way that it is ensured that the irradiation of the input device is possible only in the absence of persons in the car. For example, at least one sensor can be provided in the elevator car, with the aid of which sensor it can be determined whether persons are present in or enter the elevator car. For the detection of persons, such a sensor can contain, for example, a motion detector, a light curtain, a video camera, a light barrier, a photosensor, a light sensor, a sound sensor, a microphone or a radar sensor. This sensor or these sensors are connected to a controller for controlling the UVC radiation device. Furthermore, the controller can be designed in such a way that the UVC radiation device is at least temporarily activated during empty trips of the elevator car or in standstill phases.

Furthermore, it is conceivable to use the UVC radiation device in addition to the decontamination of the car air. The rays generated by the UVC radiation device can render viruses or other pathogens in the car air harmless.

In a first embodiment, the UVC radiation device comprises reflectors embodied as concave mirrors, wherein a reflector is preferably assigned to each radiation source. The UVC radiation device thus has a plurality of reflectors arranged next to one another. The reflector can have a preferred basic shape which is configured to collimate the UVC radiation bundle originating from the associated UVC LED and impinging on the reflector and thus to align it substantially parallel to an emission direction of the reflector. The reflector is designed and arranged in the UVC radiation device in such a way that the emission of the reflector finally impinges on the input device. The reflector can preferably be designed in such a way that the bundle of rays impinges on the car side wall virtually in a rectangular shape. This rectangle surrounds at least a portion of the surface of the input device. If a plurality of reflectors are provided, they are designed in such a way that they together cover the entire surface of the input device. In this way, efficient irradiation of the input device can be ensured. In particular, accurate irradiation is made possible with this arrangement. In addition to the input device, handrails or other surfaces that are touched more or less regularly by elevator users can be precisely irradiated for surface disinfection with an appropriate alignment of possibly additional UVC LEDs and associated reflectors.

In a preferred embodiment, the UVC LEDs can be arranged in the UVC radiation device in such a way that the emission direction of the radiation sources or UVC LEDs is directed upward or in the direction of the car ceiling. The indirect irradiation designed in this way has the advantage that focusing on the desired area is made possible.

In a particularly preferred embodiment, the UVC radiation device is designed to be low or narrow with regard to its outer dimensions. Low here means that the vertical dimension (height) of the UVC radiation device is greater than one of the horizontal dimensions (length, width), preferably each of the horizontal dimensions, of the UVC radiation device by a multiple, preferably at least two times greater, particularly preferably at least three times greater. A UVC radiation device that projects slightly downward relative to the car ceiling surface ensures optimal available space. A further advantage is that, for example, in the case of moves or transport of large goods, the UVC radiation device hardly represents a collision obstacle in the elevator car.

The UVC LEDs of the UVC radiation device can be installed in a housing or another receiving device, which is attached to the ceiling. Such a UVC radiation device allows simple retrofitting of elevator cars. However, mounting the UVC radiation device on the car ceiling so that the UVC radiation device projects downward or into the interior relative to the car ceiling surface is not absolutely necessary. It would also be conceivable to integrate the UVC radiation device in the ceiling and to thus conceal it, at least for the most part.

The UVC radiation device can comprise a housing with a one-piece housing component, to which housing component both the UVC LEDs and the reflectors are fastened. The one-piece housing component can be formed, for example, by an extruded aluminum profile or an injection-molded part made of plastic. Such a housing can be produced simply and cost-effectively.

The housing for the UVC radiation device can be box-shaped. For example, the housing could comprise a one-piece housing component with a C-profile shape. The «C», which is preferably open downward or alternatively toward the side, has an open side which forms a radiation passage opening for the UVC rays generated by the UVC LEDs and possibly deflected by the reflectors, for irradiating the input device.

A particularly compact and space-saving arrangement results when the housing has an upper housing side, which lies flat against the car ceiling, and a lower housing side, which lies opposite the upper housing side and preferably runs plane-parallel to the upper housing side. The aforementioned one-piece housing component can specify the upper housing side and the lower housing side.

If the UVC LEDs arranged next to one another are applied to a printed circuit board, it can be advantageous for the printed circuit board to be arranged at one end of a web-like projection, formed on the lower housing side, of the housing. In addition to manufacturing-related advantages, this arrangement is characterized in that the heat released by the LEDs in their chips can be dissipated in a simpler manner to the environment.

Additionally or alternatively, cooling ribs can be formed on the housing for better removal of the heat which is generated by the UVC LEDs primarily in their chips and further electronic components for operating the UVC LEDs.

According to one embodiment, the housing of the UVC radiation device can have a lower housing side which has a lamellar structure with a multiplicity of cooling ribs directed downward.

Furthermore, the UVC radiation device for closing the interior of the housing can have a transparent or at least UVC-radiation-permeable plate, which protects the UVC LEDs from dust and other external influences.

The UVC radiation device can have a plurality of radiation source rows with UVC LEDs; the rows are arranged one behind the other in a horizontal direction. The arrangement one behind the other relates to the longitudinal direction mentioned in the introduction. As a result, even comparatively large-area input devices can be efficiently irradiated and the surfaces thereof can thus be sterilized.

As an alternative to the previously described accommodation in a housing, it is also conceivable to place the UVC LEDs in an open support structure. For example, for this purpose, the aforementioned radiation source rows with the UVC LEDs can be arranged on oblique flanks, wherein for the direct irradiation of the input device by the radiation sources, the flanks are arranged in such a way that the emission direction of the radiation sources points to or is directed onto the input device.

A flat profile component with sawtooth profiling for forming the flanks for receiving the radiation source rows can be provided as the support structure. A UVC radiation device created with such a profile component is characterized by a particularly low installation height.

It can furthermore be advantageous if, in addition to the UVC LED, the radiation source has one or more further LEDs with different emission spectra, with which different color mixtures can be generated. In the activated state, the radiation source can generate a visible color, for example a red light, which serves as a warning that disinfection is currently taking place.

A further aspect of the invention relates to a UVC radiation device for irradiating an input device arranged on a first car side wall of an elevator car, with radiation in the UVC range, wherein the UVC radiation device can be arranged on a car ceiling of the elevator car, and wherein the UVC radiation device furthermore comprises a plurality of UVC LEDs as radiation sources arranged next to one another in a horizontal direction. This UVC radiation device is suitable in particular for use in the elevator car described above.

A further aspect of the invention can then be aimed at a mounting aid (e.g., a mounting template), wherein the mounting aid is matched to the radiation direction of the UVC radiation device and can be attached to the input device and indicates the mounting location for the UVC radiation device on the ceiling.

DESCRIPTION OF THE DRAWINGS

Further individual features and advantages of the invention can be derived from the following description of embodiments and from the drawings. In the drawings.

DETAILED DESCRIPTION

Figure 1:
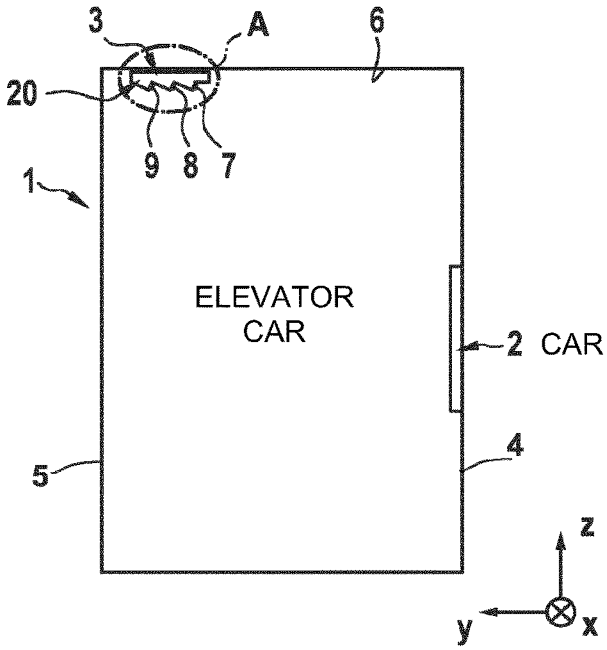
FIG. 1 is a highly simplified representation of an elevator car with a car control panel and a UVC radiation device.

FIG. 1 shows an elevator car, denoted by 1, of an elevator system fora multi-story building (not shown here). The building has an elevator shaft in which the elevator car 1 is movable vertically up and down for transporting persons or goods to individual floors. In addition to the elevator car 1, the elevator system generally has a counterweight (likewise not shown) and suspension means as well as a drive (e.g., a traction drive). The drive drives the one or more suspension means (e.g., belts or steel cables) and thus moves the elevator car 1 and the counterweight in opposite directions.

The elevator car 1 has car side walls 4, 5, a car ceiling 6 and a car floor, which together define a car interior. In conventional elevator systems, a car control panel 2 for entering a destination floor is arranged in the elevator car 1. The car control panel 2 is attached to the first car side wall denoted by 4. The car side wall opposite the first car side wall 4 is referred to below as the second car side wall 5. The distance between the two car side walls 4 and 5 is measured along a longitudinal direction, which is indicated by the arrow y. In other words, in the present document, the longitudinal direction is understood to mean the direction that extends from the first car side wall 4 equipped with the car control panel 2 to the opposite second car side wall 5. The arrow x defines a transverse direction.

In order to irradiate the car control panel 2 with radiation in the UVC range, the elevator car 1 has a UVC radiation device 3 for disinfecting the surfaces of the car control panel touched by elevator users. The UVC radiation device 3 is in this case obviously arranged on the car ceiling 6 in a rear region in the vicinity of the second car side wall 5. Instead of the car control panel 2 described here, other input devices for generating a control signal to the elevator controller could of course also be irradiated with the UVC radiation device 3 described in detail below.

The UVC radiation device 3 contains UVC LEDs 7, 8, 9 as radiation sources. The UVC LEDs 7, 8, 9 are arranged one behind the other with respect to the longitudinal direction y, wherein in the present case, the UVC radiation device 3 comprises three rows with UVC LEDs by way of example. The frontmost UVC LEDs are the UVC LEDs 7; the rearmost UVC LEDs are the UVC LEDs 9. The UVC LEDs 7, 8, 9 are arranged on a support structure 20 fastened to the car ceiling 6. This support structure 20 is a flat profile component with sawtooth profiling. The sawtooth profiling forms oblique flanks denoted by 22. The UVC LEDs 7, 8, 9 are attached to the flanks 22. For irradiating the car control panel 2 by the radiation sources or UVC LEDs 7, 8, 9, the flanks 22 are arranged in such a way that the emission direction of the UVC LEDs 7, 8, 9 is directed onto the car control panel 2. The UVC radiation device 3 can be part of a new elevator car 1. However, the UVC radiation devices 3 described here are also suitable for retrofitting already existing elevator cars 1.

If activated, the UVC LEDs 7, 8, 9 emit radiation in the UVC range between 200 and 300 nm. In this range, undesired pathogens, such as bacteria, legionellas, viruses, yeasts and fungi, on the car control panel 2 can be rendered harmless. Preferably, the UVC LEDs 7, 8, 9 emit radiation in a wavelength range between 250 nm and 280 nm, in which a particularly effective and reliable disinfection of the car control panel surfaces can be ensured. The radiation emitted by the UVC radiation device 3 in the UVC range also has a cleaning effect on the ambient air in the car interior.

The UVC LEDs 7, 8, 9, which can be seen in FIG. 1, form part of radiation source rows. The respective radiation source rows consist of a plurality of UVC LEDs which are arranged next to one another, and wherein the respective rows with the UVC LEDs 7, 8, 9 arranged next to one another extend in the x-direction.

Figure 1A:
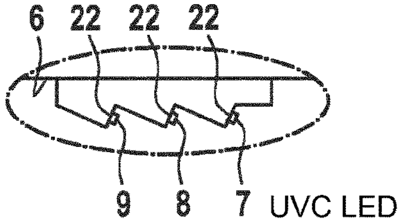
FIG. 1*a* is an enlarged representation of the UVC radiation device for irradiating the car control panel with radiation in the UVC range (detail A of FIG. 1)

It can be seen in FIG. 1*a* that the respective radiation source rows with the respective UVC LEDs 7, 8, 9 are arranged on oblique flanks 22. For direct irradiation of the car control panel 2 by the radiation sources, the flanks 22 are arranged in such a way that the emission direction of the radiation sources is directed onto the car control panel 2. The open support structure 20 is designed as a flat profile component with sawtooth profiling. The sawtooth profiling forms the flanks 22 for receiving the radiation source rows with the UVC LEDs 7, 8, 9. A “warning” feature can be provided using one or more LEDs having a different emission spectra to generate light visible to the human eye as a warning that disinfection is currently taking place. One or more of the “warning” LED can be added to the support structure 20 or substituted as one or more of the LEDs 7, 8, 9.

Figure 2:
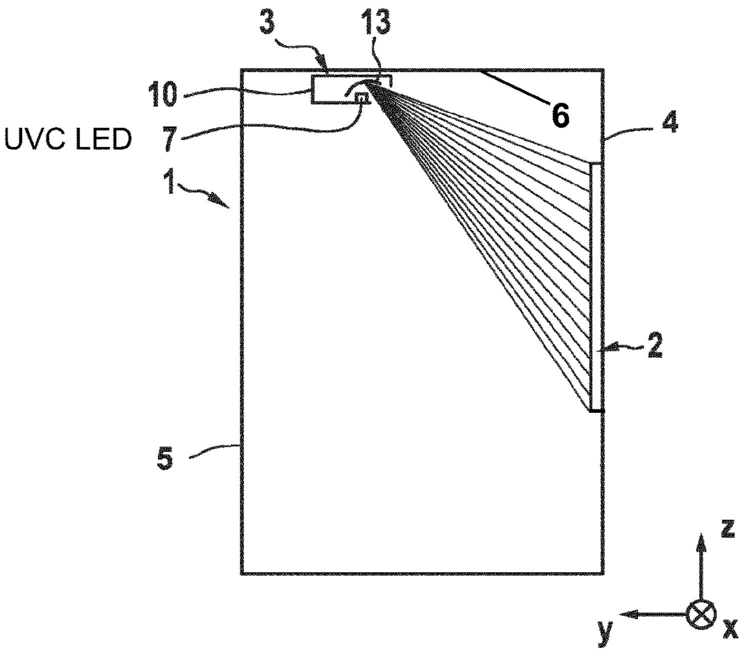
FIG. 2 is a simplified representation of an elevator car according to the invention with a car control panel and a UVC radiation device according to a second exemplary embodiment.
Figure 3:
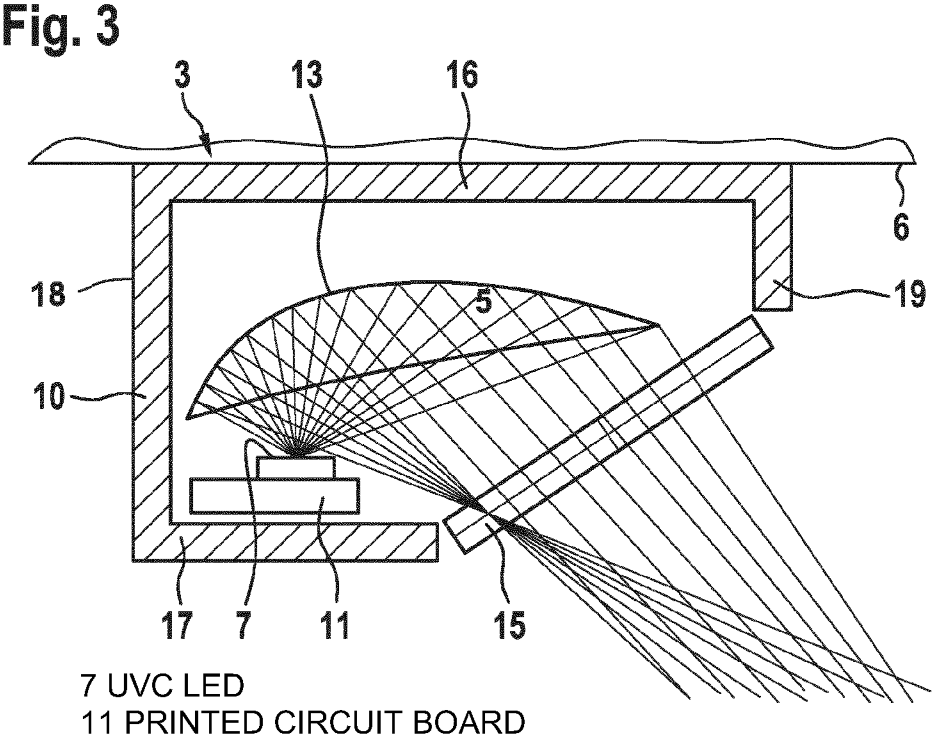
FIG. 3 is a side view of the UVC radiation device of FIG. 2.

FIG. 2 relates to a second exemplary embodiment of an elevator car 1 with an input device 2 for generating a control signal to the elevator control, such as the aforementioned car control panel for entering a destination floor, and a UVC radiation device 3 for irradiating the input device 2 with radiation in the UVC range for disinfecting the surfaces of the input device 2 touched by elevator users. The UVC radiation device 3 contains UVC LEDs 7 as radiation sources which are installed in a housing 10. The housing 10 of the UVC radiation device 3 is attached to the car ceiling 6. The UVC LEDs 7 are arranged in the UVC radiation device 3 in such a way that the emission direction of the radiation sources or UVC LEDs is directed upward. The UVC radiation device 3 furthermore has at least one reflector 13 embodied as a concave mirror. The reflector 13 is designed in such a way that the emission of the reflectors 13 impinges on the input device 2. The emission directions from the reflector 13 are indicated in the side view according to FIG. 2 by lines propagating in a fan-like manner; in the following FIG. 3, the ray directions of the UVC radiation of the UVC radiation device 3 are indicated by individual lines and can be seen even better.

The UVC radiation device 3 has a box-shaped housing 10. The housing 10 comprises an upper housing side 16, which lies flat against the car ceiling 6, and a lower housing side 17, which lies opposite the upper housing side and preferably runs plane-parallel to the upper housing side, as well as housing side walls 18, 19 running at right angles to the upper housing side 16 and lower housing side 17. For closing the interior of the housing 10, a transparent plate 15 which is permeable to UVC radiation is provided in the region of the front housing side wall 19. The UVC LEDs 7 are applied to a printed circuit board 11 which is fixed to the lower housing side 17.

Figure 4:
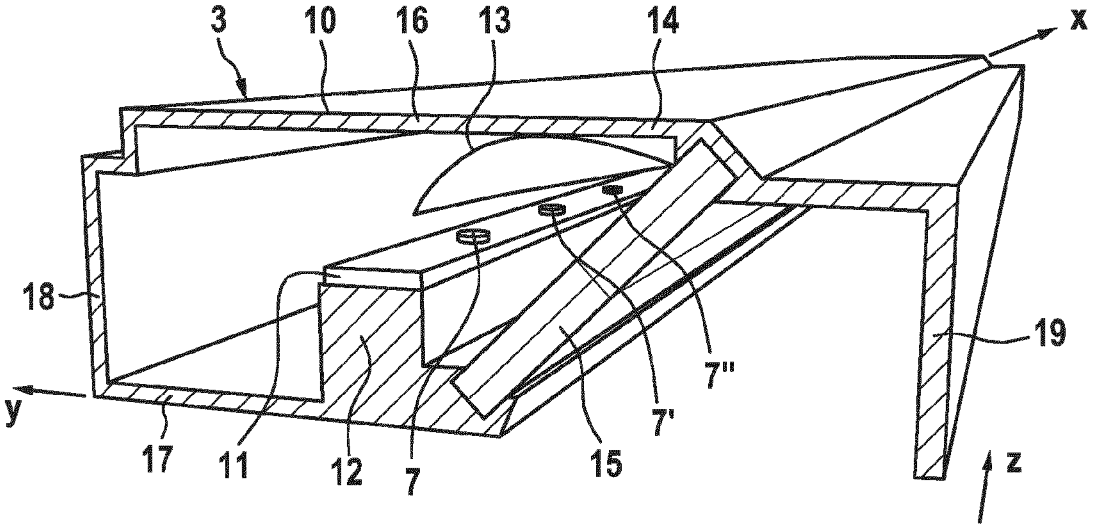
FIG. 4 is a perspective representation of a further UVC radiation device.

Construction details for a possible design of the UVC radiation device 3 are shown in FIG. 4. The housing 10 comprises a one-piece housing component 14 to which both the UVC LEDs 7 and the reflectors 13 are fastened. The housing component 14 can be formed, for example, by an extruded aluminum profile.

It can then be seen in FIG. 4 that the UVC LEDs 7 form a row which runs in the x-direction. Each row comprises a plurality of UVC LEDs which are spaced apart from one another and arranged next to one another. In the first radiation source row, the individual UVC LEDs or radiation sources are denoted by 7, 7', 7". A reflector 13 is assigned to each UVC LED 7, 7', 7".

The UVC LEDs 7, 7', 7" arranged next to one another are applied to a printed circuit board 11. A web-like projection 12 is formed on the lower housing side 17. In the present case, the printed circuit board 11 is arranged at the upper end of this web-like projection 12.

Figure 5:
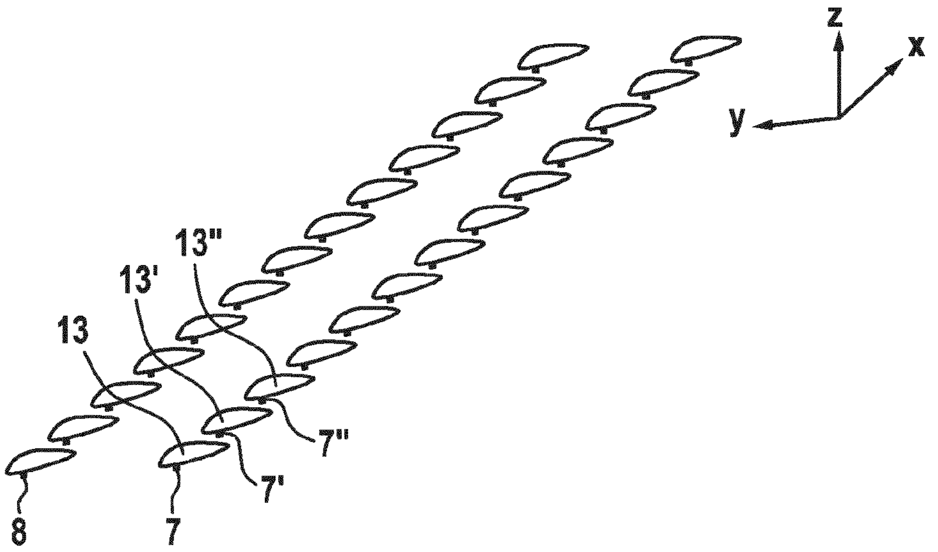
FIG. 5 is a perspective representation of UVC LEDs and associated reflectors, arranged in double rows, for a UVC radiation device for irradiating the car control panel with radiation in the UVC range.

Depending on the size of the surface of the input device 2 to be irradiated, it may be necessary to arrange more than one radiation source row in the UVC radiation device 3. Such an arrangement is shown in FIG. 5, only the radiation sources and reflectors being shown in FIG. 5 for better understanding. The housing in which the radiation sources and reflectors are accommodated is not shown. The arrangement shown here relates to a double row of radiation sources and reflectors. The first row comprises the UVC LEDs 7, 7', 7", etc. arranged next to one another. The UVC LEDs 7, 7', 7" arranged next to one another are arranged in a row at regular intervals, wherein the distance between two UVC LEDs can be at least 5 cm. The associated reflectors designed as concave mirrors are denoted by 13, 13', 13", etc. The second row with the UVC LEDs 8 is designed similarly.

Figure 6:
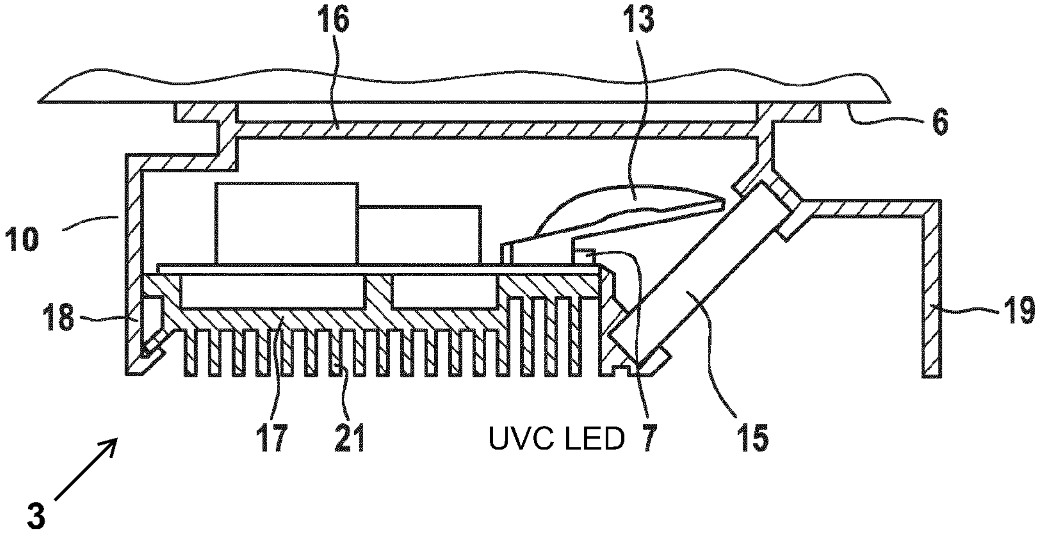
FIG. 6 is a side view of a further UVC radiation device for irradiating the car control panel with radiation in the UVC range.

FIG. 6 shows a further UVC radiation device 3 for irradiating the input device 2 with radiation in the UVC range for disinfecting the surfaces touched by elevator users. This UVC radiation device 3 essentially differs from the UVC radiation device shown in FIG. 4 by a different design of the housing 10. Here, the housing 10 is designed in several parts. For removing the heat generated by the UVC LEDs 7 in their chips and further electronic components for operating the UVC LEDs 7, cooling ribs 21 are formed on the housing 10. For this purpose, the housing 10 has a lower housing side 17 with a lamellar structure. This lamellar structure is formed by a plurality of downward directed cooling ribs 21.

In accordance with the provisions of the patent statutes, the present invention has been described in what is considered to represent its preferred embodiment. However, it should be noted that the invention can be practiced otherwise than as specifically illustrated and described without departing from its spirit or scope.

The invention claimed is:

1. An elevator car comprising:

an input device arranged on a first car side wall in an interior of the elevator car;

a UVC radiation device arranged on a car ceiling in the interior of the elevator car;

wherein the UVC radiation device is adapted to irradiate the input device with radiation in a UVC range from a plurality of radiation sources;

wherein the UVC radiation device includes a plurality of UVC LEDs arranged next to one another in a horizontal direction and emitting the radiation as the radiation sources; and wherein the UVC LEDs are further arranged in a plurality of radiation source rows, each of the source rows being arranged on an associated one of a plurality of oblique flanks of a support structure, the oblique flanks being arranged such that an emission direction of the UVC LEDs is directed onto the input device.

2. The elevator car according to claim 1 wherein the UVC radiation device includes a plurality of reflectors embodied as concave mirrors and directing the radiation toward the input device.

3. The elevator car according to claim 2 wherein each of the reflectors is associated with one of the UVC LEDs.

4. The elevator car according to claim 1 wherein each of the UVC LEDs is arranged in the UVC radiation device to emit the radiation in an emission direction directed upward toward the car ceiling.

5. The elevator car according to claim 1 wherein the UVC LEDs are installed in a box-shaped housing that is attached to the car ceiling.

6. The elevator car according to claim 5 wherein the housing is a one-piece housing component, and wherein the UVC LEDs and a plurality of reflectors are fastened to the housing component.

7. The elevator car according to claim 5 wherein the housing has an upper housing side that lies flat against the car ceiling and a lower housing side that is opposite the upper housing side and runs plane-parallel to the upper housing side.

8. The elevator car according to claim 5 wherein the UVC LEDs are applied to a printed circuit board that is arranged at one end of a web-like projection formed on a lower housing side of the housing.

9. The elevator car according to claim 5 wherein the UVC radiation device includes a transparent plate closing an interior of the box-shaped housing.

10. The elevator car according to claim 1 wherein the UVC radiation device has a housing with a lower housing side, the lower housing side having a lamellar structure with a multiplicity of downward directed cooling ribs.

11. The elevator car according to claim 1 wherein the UVC LEDs are arranged in at least two radiation source rows, the at least two radiation source rows being arranged one behind the other in the horizontal direction.

12. The elevator system according to claim 1 wherein the support structure includes a flat profile component with sawtooth profiling forming the oblique flanks.

13. The elevator car according to claim 1 wherein the UVC radiation device includes at least one LED having a different emission spectra from the UVC LEDs and adapted to generate light visible to a human eye.

14. A UVC radiation device for an elevator car, the device comprising:

a support structure adapted to be arranged on a car ceiling in an interior of the elevator car;

the support structure having a plurality of oblique flanks arranged next to one another in a horizontal direction; and a plurality of UVC LEDs emitting UVC radiation, the UVC LEDs being arranged next to one another in radiation source rows, each of the source rows being arranged on an associated one of the oblique flanks such that when the support structure is arranged on the car ceiling, an emission direction of the UVC LEDs is directed onto an input device arranged on a car side wall in the interior of the elevator car.

* * * * *